US012254553B2

(12) United States Patent
Kudo et al.

(10) Patent No.: US 12,254,553 B2
(45) Date of Patent: Mar. 18, 2025

(54) LEARNING DEVICE, LEARNING METHOD, LEARNING PROGRAM, IMAGE GENERATION DEVICE, IMAGE GENERATION METHOD, IMAGE GENERATION PROGRAM, AND IMAGE GENERATION MODEL

(71) Applicant: FUJIFILM Corporation, Tokyo (JP)

(72) Inventors: Akira Kudo, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 484 days.

(21) Appl. No.: 17/692,172

(22) Filed: Mar. 11, 2022

(65) Prior Publication Data

US 2022/0198734 A1    Jun. 23, 2022

Related U.S. Application Data

(63) Continuation of application No. PCT/JP2020/037299, filed on Sep. 30, 2020.

(30) Foreign Application Priority Data

Sep. 30, 2019   (JP) ................................. 2019-179044

(51) Int. Cl.
*G06T 15/00*    (2011.01)
*G06T 3/4046*   (2024.01)

(52) U.S. Cl.
CPC ............ *G06T 15/00* (2013.01); *G06T 3/4046* (2013.01); *G06T 2210/41* (2013.01)

(58) Field of Classification Search
CPC ... G06T 15/00; G06T 3/4046; G06T 2210/41; G06T 17/00; G06T 19/006;
(Continued)

(56) References Cited

U.S. PATENT DOCUMENTS

2017/0103287 A1    4/2017  Han
2017/0278289 A1*   9/2017  Marino .................. G06T 7/536
(Continued)

FOREIGN PATENT DOCUMENTS

| JP | 2018505705 | 3/2018 |
| JP | 2018192264 | 12/2018 |
| JP | 2018535732 | 12/2018 |

OTHER PUBLICATIONS

Cheng-Bin Jin et al., "Deep CT to MR Synthesis Using Paired and Unpaired Data," Sensors, May 2019, pp. 1-19.
(Continued)

*Primary Examiner* — Nimesh Patel
(74) *Attorney, Agent, or Firm* — JCIPRNET

(57) ABSTRACT

An image generation device derives, for a subject including a specific structure, a subject model representing the subject by deriving each feature amount of the target image having the at least one representation format and combining the feature amounts based on the target image. A latent variable derivation unit derives a latent variable obtained by dimensionally compressing a feature of the subject model according to the target information based on the target information and the subject model. A virtual image derivation unit outputs a virtual image having the representation format represented by the target information based on the target information, the subject model, and the latent variable.

10 Claims, 11 Drawing Sheets

(58) Field of Classification Search
CPC . G06T 2207/20081; G06T 2207/20084; G06T 7/70; G06T 7/0004; G06T 2207/10016; G06T 11/00; G06T 19/00; G06T 2207/20221; G06T 7/0012; G06T 7/75; G06T 2207/30196; G06T 7/11; G06T 5/60; G06T 7/00; G06T 7/246; G06T 13/40; G06T 2207/10004; G06T 2210/56; G06T 7/001; G06T 1/00; G06T 2200/28; G06T 2219/004; G06T 7/73; G06T 13/20; G06T 15/005; G06T 7/20; G06T 7/60; G06T 7/74; G06T 2210/12; G06T 3/40; G06T 3/04; G06T 3/00; G06T 7/30; G06T 7/55; G06T 9/001; G06T 9/002; G06T 2207/10024; G06T 7/0014; G06T 2207/10088; G06T 2207/20072; G06T 7/0002; G06T 17/05; G06T 2207/30168; G06T 7/0008; G06T 7/33; G06T 7/41; G06T 9/008; G06T 15/04; G06T 15/08; G06T 9/00; G06T 7/50; G06T 15/20; G06T 2207/10056; G06T 19/20; G06T 2200/08; G06T 2207/10081; G06T 3/4038; G06T 5/50; G06T 1/20; G06T 19/003; G06T 2207/10028; G06T 3/4053; G06T 7/85; G06T 1/0007; G06T 2219/2021; G06T 2219/2004; G06T 7/251; G06N 3/045; G06N 3/08; G06N 20/00; G06N 3/0464; G06N 3/044; G06N 3/0455; G06N 5/02; G06N 3/02; G06N 3/048; G06N 3/088; G06N 3/09; G06N 3/0475; G06N 3/094; G06N 7/01; G06N 3/082; G06N 3/084; G06N 20/20; G06N 5/01; G06N 5/022; G06N 3/063; G16H 50/00; A61B 5/055; A61B 6/03; A61B 34/20; A61B 34/10; A61B 5/117; A61B 2034/105; A61B 2090/364; A61B 1/000096; A61B 2090/365; A61B 5/742; G06F 3/011; G06F 21/32; G06F 18/214; G06F 18/22; G06F 3/14; G06F 2203/011; G06F 18/24; G06F 3/147; G06F 3/04845; G06F 16/436; G06F 16/906; G06F 18/23; G06F 18/2431; G06F 30/27; G06F 2218/12; G06F 40/20; G06F 9/3001; G06F 18/213; G06F 16/55; G06F 16/289; G06V 40/171; G06V 40/166; G06V 10/82; G06V 40/172; G06V 40/174; G06V 40/176; G06V 10/764; G06V 40/16; G06V 20/50; G06V 20/20; G06V 40/70; G06V 40/168; G06V 10/145; G06V 20/64; G06V 20/647; G06V 40/165; G06V 40/20; G06V 10/40; G06V 10/7715; G06V 40/10; G06V 10/74; G06V 10/757; G06V 10/761; G06V 20/58; G06V 2201/05; G06V 40/1365; G06V 20/698; G06V 10/50; G06V 10/774; G06V 30/19173; G06V 10/806; G06V 2201/03; G06V 10/44; G06V 10/462; G06V 2201/07; G06V 40/23; G06V 40/28; G06V 20/52; G06V 2201/08; G06V 2201/12; G06Q 20/40145; H04L 63/0861; H04L 63/108; H04L 67/535; G16B 20/00; G16B 40/00; G16B 40/20; G16B 40/30; G16B 5/00
See application file for complete search history.

(56) References Cited

U.S. PATENT DOCUMENTS

| | | | | |
|---|---|---|---|---|
| 2017/0372497 | A1* | 12/2017 | Hu | G06T 5/90 |
| 2018/0336677 | A1* | 11/2018 | Sloan | G06T 7/0012 |
| 2019/0042885 | A1* | 2/2019 | Han | G06T 7/0012 |
| 2022/0004803 | A1* | 1/2022 | Li | G06T 19/006 |
| 2023/0132630 | A1* | 5/2023 | Kang | G06N 3/045 |
| | | | | 706/15 |

OTHER PUBLICATIONS

Yunjey Choi et al., "StarGAN: Unified Generative Adversarial Networks for Multi-Domain Image-to-Image Translation," arXiv:1711.09020v3 [cs.CV], Sep. 2018, pp. 1-15.

S.M. Ali Eslami et al., "Neural scene representation and rendering," Science, vol. 360, Jun. 2018, pp. 1204-1210.

"International Search Report (Form PCT/ISA/210) of PCT/JP2020/037299," mailed on Nov. 24, 2020, with English translation thereof, pp. 1-4.

"Written Opinion of the International Searching Authority (Form PCT/ISA/237)" of PCT/JP2020/037299, mailed on Nov. 24, 2020, with English translation thereof, pp. 1-6.

* cited by examiner

LEARNING DEVICE, LEARNING METHOD, LEARNING PROGRAM, IMAGE GENERATION DEVICE, IMAGE GENERATION METHOD, IMAGE GENERATION PROGRAM, AND IMAGE GENERATION MODEL

CROSS REFERENCE TO RELATED APPLICATIONS

The present application is a Continuation of PCT International Application No. PCT/JP2020/037299, filed on Sep. 30, 2020, which claims priority to Japanese Patent Application No. 2019-179044, filed on Sep. 30, 2019. Each application above is hereby expressly incorporated by reference, in its entirety, into the present application.

BACKGROUND

Technical Field

The present disclosure relates to a learning device of an image generation model, a learning method, a learning program, an image generation device, an image generation method, an image generation program, and an image generation model, which derive a virtual image having a target representation format from a target image.

Related Art

In a medical field, advances in various modalities, such as a computed tomography (CT) apparatus and a magnetic resonance imaging (MRI) apparatus, have made it is possible to perform image diagnosis by using a medical image having a higher quality. In addition, with the recent progress of artificial intelligence (AI) technology, it has been proposed to convert an image of a certain domain into an image of a different domain by using a conversion model including a neural network or the like that is trained through machine learning. For example, JP2018-535732A proposes a method of using a plurality of sets of MRI images and CT images and generating a model that outputs a virtual CT image in a case in which an MRI image is input. In addition, Cheng-Bin Jin, Hakil Kim, Wonmo Jung, Seongsu Joo, Ensik Park, Ahn Young Saem, In Ho Han, Jae Il Lee, Xuenan Cui "Deep CT to MR Synthesis using Paired and Unpaired Data", Sensors 2019.19(10), 2361 proposes a method of using a set of a CT image and a T2-weighted image of MRI as teacher data and generating a model that outputs the T2-weighted image of MRI in a case in which the CT image is input.

In addition, a generative adversarial network (GAN) that alternately learns a "generator" which produces data and a "discriminator" which identifies the data has been proposed. For example, Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv:1711.09020 proposes a network that uses a single generator and discriminator and realizes multimodal domain conversion. In the method described in Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv:1711.09020, Various target facial expressions (for example, blonde hair, black hair, smiling face, angry face, and the like) of an image to be converted (for example, a facial image of a person) are given to the input of the generator at the same time as a domain label, in the discriminator, the domain, that is, the facial expression is determined as well as the authenticity of the input image, and the generator and the discriminator are trained.

In addition, S. M. Ali Eslami et al., "Neural scene representation and rendering", DeepMind, 5 New Street Square, London EC4A 3TW, UK. proposes a method of using an image obtained by imaging a scene from a plurality of viewpoints and generating an image captured from an unknown viewpoint. In the method described in S. M. Ali Eslami et al., "Neural scene representation and rendering", DeepMind, 5 New Street Square, London EC4A 3TW, UK., a representation network and a generation network are prepared, a feature amount is extracted from the image obtained by imaging a certain scene from the plurality of viewpoints in the representation network, and a scene model that outputs an image of an unknown target viewpoint from the feature amount is generated. Moreover, in the generation network, an image viewed from an unknown viewpoint is generated based on the scene model and the unknown target viewpoint.

However, in the methods described in JP2018-535732A and Cheng-Bin Jin, Hakil Kim, Wonmo Jung, Seongsu Joo, Ensik Park, Ahn Young Saem, In Ho Han, Jae Il Lee, Xuenan Cui "Deep CT to MR Synthesis using Paired and Unpaired Data", Sensors 2019.19(10), 2361, only the image having the representation format used in a case of learning the model can be generated. For example, in the method described in JP2018-535732A, only the CT image can be generated by inputting the MRI image. In addition, in the method described in Cheng-Bin Jin, Hakil Kim, Wonmo Jung, Seongsu Joo, Ensik Park, Ahn Young Saem, In Ho Han, Jae Il Lee, Xuenan Cui "Deep CT to MR Synthesis using Paired and Unpaired Data", Sensors 2019.19(10), 2361, only the T2-weighted image of MRI can be generated by inputting the CT image. In addition, in the method described in Yunjey Choi, Minje Choi, Munyoung Kim, Jung-Woo Ha, Sunghun Kim, Jaegul Choo "StarGAN: Unified Generative Adversarial Networks for Multi-Domain Image-to-Image Translation", arXiv:1711.09020, there is a possibility that a unique feature of the representation format of the input image is lost in a case of conversion of the representation format. In addition, in the method described in S. M. Ali Eslami et al., "Neural scene representation and rendering", DeepMind, 5 New Street Square, London EC4A 3TW, UK., processing is limited to scene recognition.

SUMMARY

The present disclosure has been made in view of the above circumstances, and is to enable the generation of an image in a target representation format.

The present disclosure relates to a learning device of an image generation model that, in a case in which at least one target image for a subject, which includes a specific structure, having at least one representation format, and target information representing a target representation format of the target image are input, derives a virtual image having the target representation format from the target image, in which the image generation model includes a first network that outputs a subject model representing the subject by deriving each feature amount of the target image having the at least one representation format and combining the feature amounts by inputting the target image, a second network that, in a case in which the target information and the subject model are input, outputs a latent variable obtained by dimensionally compressing a feature of the subject model according to the target information, and a third network that, in a case in which the target information, the subject model, and the latent variable are input, outputs the virtual image, and the learning device comprises a learning unit that trains the first network, the second network, and the third network based on a plurality of teacher images having different representation formats for the subject including the specific structure, and a plurality of teacher data including specific teacher information representing a specific representation format among representation formats of the plurality of teacher images.

Note that, in the learning device according to the present disclosure, the first network may output the subject model representing the subject by deriving each feature amount of the target image and combining the feature amounts by inputting information representing the representation format of the target image in addition to the target image.

In addition, the learning device according to the present disclosure may further comprise a fourth network that, in a case in which an image is input, outputs a latent variable obtained by dimensionally compressing a feature of the image, in which the learning unit inputs another teacher image having a representation format other than the specific representation format among the plurality of teacher images included in the teacher data to the first network to output a teacher subject model, inputs the specific teacher information and the teacher subject model to the second network to output a first teacher latent variable obtained by dimensionally compressing a feature of the teacher subject model according to the specific teacher information, inputs a specific teacher image having the specific representation format to the fourth network to output a second teacher latent variable obtained by dimensionally compressing a feature of the specific teacher image, and trains the first network and the second network by using a difference between the first teacher latent variable and the second teacher latent variable as a first loss.

In addition, in the learning device according to the present disclosure, the learning unit may input the specific teacher information, the teacher subject model, and the first teacher latent variable to the third network to output a teacher virtual image having the specific representation format, and learn the first network, the second network, and the third network by using a difference between the teacher virtual image and the specific teacher image as a second loss.

In addition, in the learning device according to the present disclosure, the target information may represent at least one of a type of image, presence or absence of a contrast medium, a contrast phase in a case in which a contrast medium is present, time before and after current time, gender of the subject, or age of the subject as the representation format.

In addition, in the learning device according to the present disclosure, the target image may be a three-dimensional medical image, and the representation format may include at least one type of image of a CT image, an MRI image, or a PET image.

In this case, the type of image may include at least one of a T1-weighted image, a T2-weighted image, a diffusion-weighted image, a fat suppression image, an FLAIR image, a pre-contrast T1-weighted image, a post-contrast T1-weighted image, a T1-weighted image (in phase), a T1-weighted image (out phase), or a T2-fat suppression image in the MRI image.

The present disclosure relates to an image generation device that, in a case in which at least one target image for a subject, which includes a specific structure, having at least one representation format and target information representing a target representation format of the target image are input, derives a virtual image having the target representation format from the target image, the image generation device comprising a subject model derivation unit that derives a subject model representing the subject by deriving each feature amount of the target image having the at least one representation format and combining the feature amounts based on the target image, a latent variable derivation unit that derives a latent variable obtained by dimensionally compressing a feature of the subject model according to the target information based on the target information and the subject model, and a virtual image derivation unit that derives the virtual image based on the target information, the subject model, and the latent variable.

Note that, in the image generation device according to the present disclosure, the subject model derivation unit may derive the subject model representing the subject by deriving each feature amount of the target image and combining the feature amounts based on information representing the representation format of the target image in addition to the target image.

In addition, in the image generation device according to the present disclosure, the subject model derivation unit, the latent variable derivation unit, and the virtual image derivation unit may include a first network, a second network, and a third network trained by the learning device of the image generation model according to the present disclosure, respectively.

The present disclosure relates to an image generation model trained by the learning device according to the present disclosure.

The present disclosure relates to a learning method of an image generation model that, in a case in which at least one target image for a subject, which includes a specific structure, having at least one representation format, and target information representing a target representation format of the target image are input, derives a virtual image having the target representation format from the target image, in which the image generation model includes a first network that outputs a subject model representing the subject by deriving each feature amount of the target image having the at least one representation format and combining the feature amounts by inputting the target image, a second network that, in a case in which the target information and the subject model are input, outputs a latent variable obtained by dimensionally compressing a feature of the subject model according to the target information, and a third network that, in a case in which the target information, the subject model, and the latent variable are input, outputs the virtual image, and the learning method comprises learning the first network, the second network, and the third network based on a plurality of teacher images having different representation formats for the subject including the specific structure, and a plurality of teacher data including specific teacher information representing a specific representation format among representation formats of the plurality of teacher images.

The present disclosure relates to an image generation method of, in a case in which at least one target image for a subject, which includes a specific structure, having at least one representation format and target information representing a target representation format of the target image are input, deriving a virtual image having the target representation format from the target image, the image generation method comprising deriving a subject model representing the subject by deriving each feature amount of the target image having the at least one representation format and combining the feature amounts based on the target image, deriving a latent variable obtained by dimensionally compressing a feature of the subject model according to the target information based on the target information and the subject model, and deriving the virtual image based on the target information, the subject model, and the latent variable.

Note that the learning method of the image generation model and the image generation method according to the present disclosure may be provided as programs to be executed by a computer.

The present disclosure relates to a learning device of an image generation model that, in a case in which at least one target image for a subject, which includes a specific structure, having at least one representation format, and target information representing a target representation format of the target image are input, derives a virtual image having the target representation format from the target image, the learning device comprising a memory that stores an instruction to be executed by a computer, and a processor configured to execute the stored instruction, in which the image generation model includes a first network that outputs a subject model representing the subject by deriving each feature amount of the target image having the at least one representation format and combining the feature amounts by inputting the target image, a second network that, in a case in which the target information and the subject model are input, outputs a latent variable obtained by dimensionally compressing a feature of the subject model according to the target information, and a third network that, in a case in which the target information, the subject model, and the latent variable are input, outputs the virtual image, and the processor executes processing of learning the first network, the second network, and the third network based on a plurality of teacher images having different representation formats for the subject including the specific structure, and a plurality of teacher data including specific teacher information representing a specific representation format among representation formats of the plurality of teacher images.

The present disclosure relates to another image generation device that, in a case in which at least one target image for a subject, which includes a specific structure, having at least one representation format and target information representing a target representation format of the target image are input, derives a virtual image having the target representation format from the target image, the image generation device comprising a memory that stores an instruction to be executed by a computer, and a processor configured to execute the stored instruction, in which the processor executes processing of deriving a subject model representing the subject by deriving each feature amount of the target image having the at least one representation format and combining the feature amounts based on the target image, deriving a latent variable obtained by dimensionally compressing a feature of the subject model according to the target information based on the target information and the subject model, and deriving the virtual image based on the target information, the subject model, and the latent variable.

According to the present disclosure, it is possible to generate a virtual image having a target representation format from a target image.

DETAILED DESCRIPTION

Figure 1:
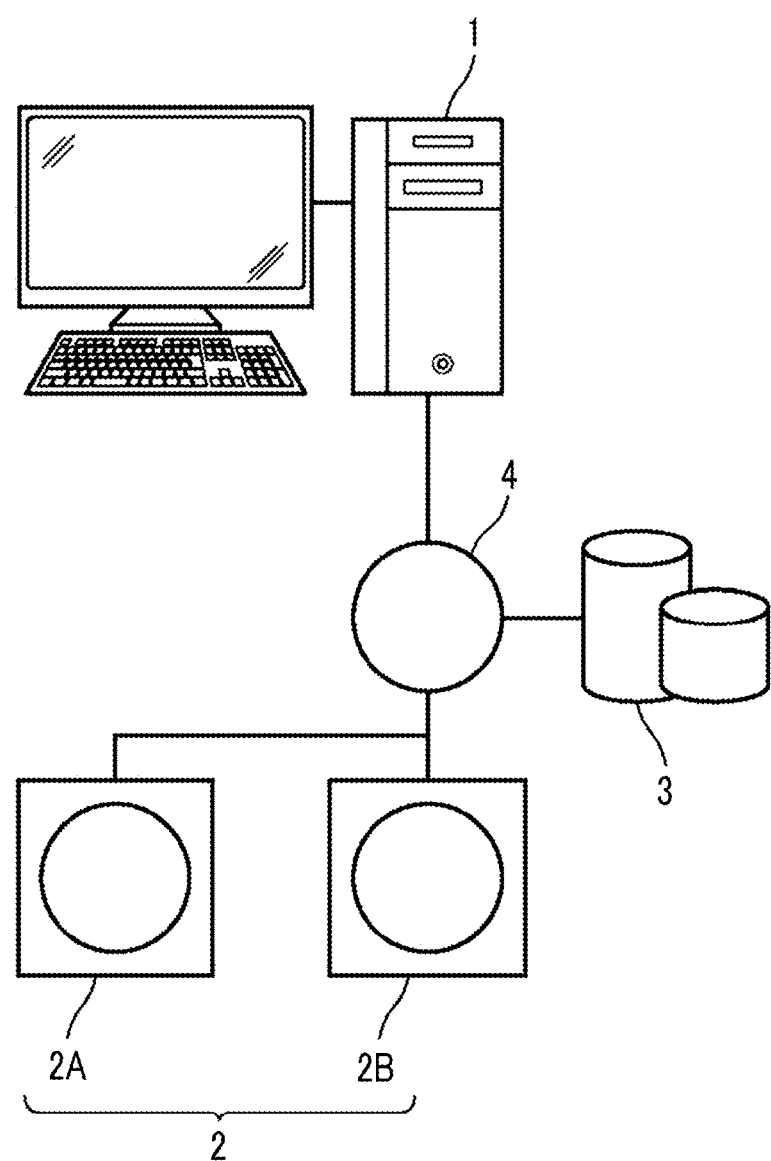
FIG. 1 is a hardware configuration diagram showing an outline of a diagnosis support system to which a learning device and an image generation device according to an embodiment of the present disclosure are applied.

In the following, an embodiment of the present disclosure will be described with reference to the drawings. FIG. 1 is a hardware configuration diagram showing an outline of a diagnosis support system to which a learning device and an image generation device according to the embodiment of the present disclosure are applied. As shown in FIG. 1, in the diagnosis support system, the learning device and the image generation device (hereinafter, represented by an image processing device) 1 according to the present embodiment, a modality 2, and an image storage server 3 are connected in a communicable state via a communication network 4.

The modality 2 is an apparatus that images a site including a diagnosis target structure of a human as a subject to generate a three-dimensional image representing the diagnosis target site, and specifically, is a CT apparatus, an MRI apparatus, a positron emission tomography (PET) apparatus, and the like. The three-dimensional image including of a plurality of slice images generated by the modality 2 is transmitted to and stored in the image storage server 3. Note that in the present embodiment, it is assumed that the modality 2 includes a CT apparatus 2A and an MRI apparatus 2B. It is assumed that the CT apparatus 2A and the MRI apparatus 2B can inject a contrast medium into a blood vessel of a patient and perform contrast imaging for confirming the spread of the contrast medium. In addition, it is assumed that the MRI apparatus 2B can generate an MRI image having any representation format, such as a T1-weighted image and a T2-weighted image.

Here, in a medical image, a representation format of the image differs in a case in which a type of image is different, such as the CT image and the MRI image. For example, even in a case in which a tissue of a human body included in the image is the same, the density differs between the CT image and the MRI image. In addition, even in a case in which the same MRI image is used, the representation format differs between the T1-weighted image and the T2-weighted image. Specifically, on the T1-weighted image, mostly, a fat tissue appears white, water, a humoral component, and a cyst appear black, and a tumor appears slightly black. In addition, on the T2-weighted image, water, a humoral component, and a cyst appear white, as well as the fat tissue. Therefore, the CT image, the T1-weighted image, and the T2-weighted image are images having different representation formats, respectively.

In addition, depending on the presence or absence of the contrast medium, the appearance of the image differs between the CT image acquired by performing imaging by using the contrast medium and a non-contrast CT image acquired by performing imaging without using the contrast medium. Therefore, the representation format of the image differs depending on the presence or absence of the contrast medium. In addition, in a case in which the image is captured by using the contrast medium, the spread of the contrast medium is changed with the elapse of time. Therefore, the representation format of the image differs depending on an elapsed time (contrast phase) after the contrast medium is injected. In addition, since the size, the density, and the like of an abnormal site are changed with the elapse of time, the appearance of the abnormal site, such as a lesion included in the same structural part of the same subject, is different. Therefore, the representation format of the image differs in the time before and after the current time.

The image storage server 3 is a computer that stores and manages various data, and comprises a large capacity external storage device and software for database management. The image storage server 3 performs communication with other devices via the wired or wireless communication network 4 to transmit and receive image data and the like. Specifically, the image storage server 3 acquires various data including the image data of a medical image generated by the modality 2 via the network, and stores and manages the image data in a recording medium, such as the large capacity external storage device. Note that a storage format of the image data and the communication between the devices via the communication network 4 are based on a protocol, such as digital imaging and communication in medicine (DI-COM). In addition, in the present embodiment, the image storage server 3 also stores and manages a plurality of teacher data to be described below.

The image generation device 1 including the learning device according to the present embodiment is a computer in which an image generation program and a learning program according to the present embodiment are installed. The computer may be a workstation or a personal computer directly operated by a doctor who makes a diagnosis, or a server computer connected to the workstation or the personal computer via the network. Alternatively, the image generation program and the learning program are stored in a storage device of the server computer connected to the network or a network storage in a state of being accessible from the outside, and are downloaded and installed in the computer used by the doctor in response to a request. Alternatively, the image processing program and the learning program are distributed in a state of being recorded on a recording medium, such as a digital versatile disc (DVD) or a compact disc read only memory (CD-ROM), and are installed in the computer from the recording medium.

Figure 2:
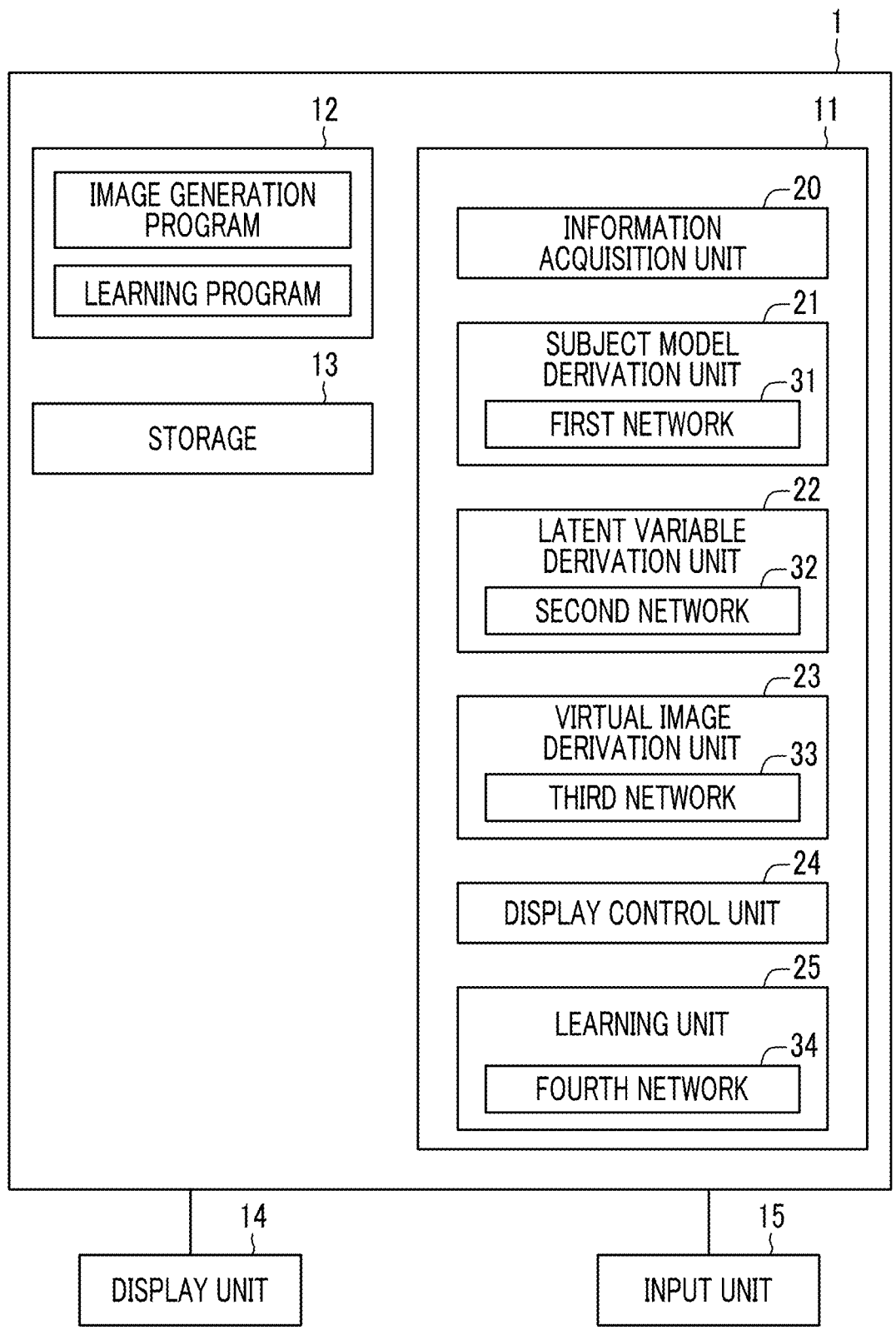
FIG. 2 is a diagram showing a schematic configuration of the image generation device according to the embodiment of the present disclosure.

FIG. 2 is a diagram showing a schematic configuration of the image generation device realized by installing the image generation program and the learning program in the computer. As shown in FIG. 2, the image generation device 1 comprises a central processing unit (CPU) 11, a memory 12, and a storage 13, as a configuration of a standard workstation. In addition, the image generation device 1 is connected with a display unit 14, such as a liquid crystal display, and an input unit 15, such as a keyboard or a mouse.

The storage 13 is configured by a hard disk drive or the like, and stores various pieces of information including at least one target image, which is a generation target of the virtual image, the teacher data for learning the network configuring the image generation device as described below, and information necessary for processing, which are acquired from the image storage server 3 via the communication network 4.

In addition, the image generation program and the learning program are stored in the memory 12. The image generation program causes the CPU 11 to execute image generation processing of, in a case in which at least one target image for the subject, which includes a specific structure, having at least one representation format and target information representing a target representation format of the target image are input, deriving the virtual image having the target representation format from the target image. Specifically, the image generation program defines, as processing to be executed by the CPU 11, information acquisition processing of acquiring at least one target image and the target information, subject model derivation processing of deriving the subject model representing the subject by deriving the feature amount from at least one target image and combining the feature amounts, latent variable derivation processing of deriving a latent variable obtained by dimensionally compressing a feature of the subject model according to the target information based on the target information and the subject model, virtual image derivation processing of deriving the virtual image having the target representation format based on the target information, the subject model, and the latent variable, and display control processing of displaying the virtual image on the display unit 14.

As the processing to be executed by the CPU 11, the learning program defines an information acquisition processing of acquiring various pieces of information including the teacher data for learning an image generation model included in the image generation device, and a learning processing of learning the image generation model.

Moreover, the CPU 11 executes the processing according to the image generation program and the learning program, so that the computer functions as an information acquisition unit 20, a subject model derivation unit 21, a latent variable derivation unit 22, a virtual image derivation unit 23, a display control unit 24, and a learning unit 25.

The information acquisition unit 20 acquires information ti representing the representation format for each of at least one target image $Gi$ ($i=1$ to $n$) having at least one representation format and a target image $Gi$ from the image storage server 3 via an interface (not shown) connected to the communication network 4. In addition, the information acquisition unit 20 acquires target information $A0$ representing the target representation format of the target image $Gi$ by input from the input unit 15 or the like. In addition, the information acquisition unit 20 acquires a plurality of teacher images having different representation formats for the subject including the specific structure, and a plurality of teacher data including specific teacher information representing the specific representation format among the representation formats of the plurality of teacher images. Note that in a case in which a plurality of the target images $Gi$ are used in one processing, the plurality of target images Gi input to the image generation device 1 are images including the same structure for the same patient and having different representation formats. In addition, the target information A0 is information representing the target representation format of a virtual image V0 to be generated. As the target representation format, for example, at least one of the type of image, the presence or absence of the contrast medium, the contrast phase, or the time before and after the current time can be used.

Here, the specific structure of the subject included in the target image and the teacher image is the same structure. For example, in a case in which the structure included in the target image is the liver, the structure included in the teacher image is also the liver. In the following, the specific structure will be described as being the liver.

The subject model derivation unit 21 derives a subject model M0 representing the specific structure in the subject by deriving the feature amounts and combining the feature amounts based on the target image Gi and the information ti representing the representation format of the target image Gi. Therefore, the subject model derivation unit 21 includes a first network 31 that outputs the subject model M0 representing the subject by deriving the feature amount of the input target image Gi in a case in which at least one target image Gi and the information ti representing the representation format of the target image Gi are input, further combining a plurality of feature amounts in a case in which the plurality of target images Gi are input and the plurality of feature amounts are derived. In the present embodiment, since the subject is the human body, the subject model M0 can be said to be a human body model.

The latent variable derivation unit 22 derives a latent variable z1 obtained by dimensionally compressing a feature of the subject model M0 according to the target information A0 based on the target information A0 and the subject model M0. For this purpose, the latent variable derivation unit 22 includes a second network 32 that outputs the latent variable z1 in a case in which the target information A0 and the subject model M0 are input. The latent variable z1 will be described below.

The virtual image derivation unit 23 derives the virtual image V0 having the target representation format represented by the target information A0 based on the target information A0, the subject model M0, and the latent variable z1. For this purpose, the virtual image derivation unit 23 includes a third network 33 that derives the virtual image V0 in a case in which the target information A0, the subject model M0, and the latent variable z1 are input.

Figure 3:
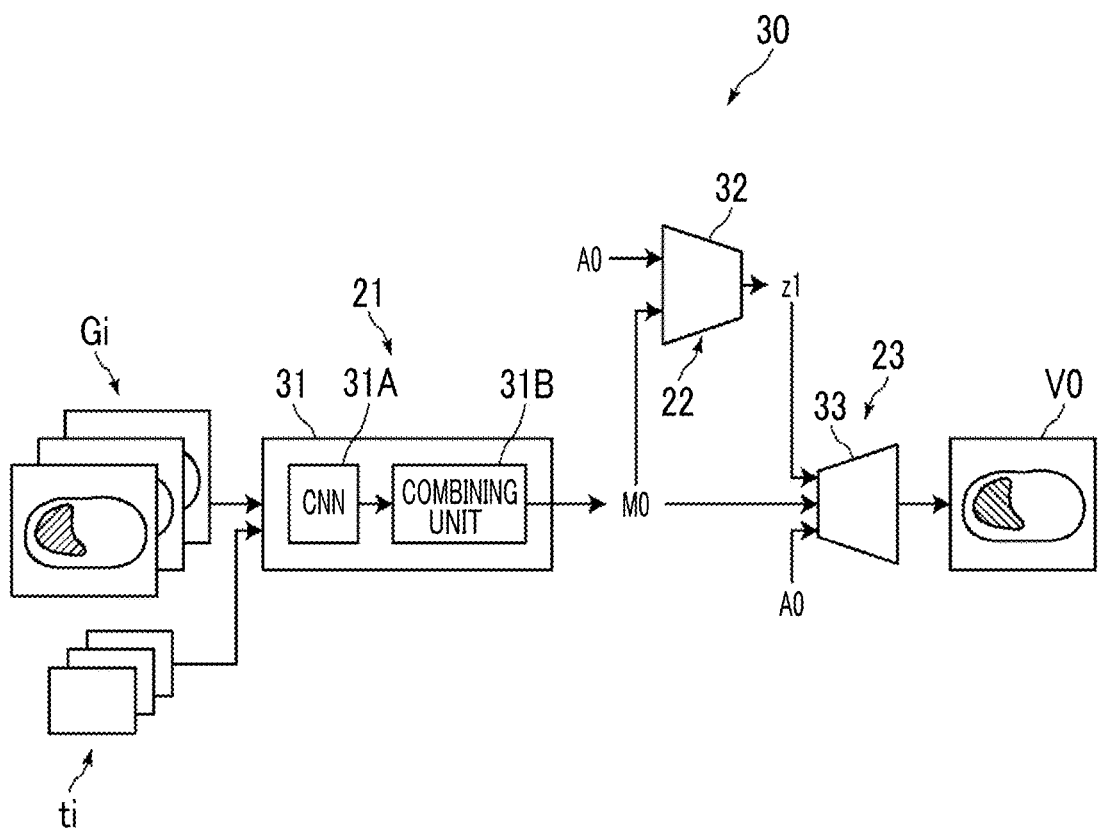
FIG. 3 is a schematic diagram showing a configuration of an image generation model.

Note that, in FIG. 3, the first network 31, the second network 32, and the third network 33 are separately shown as being included in the subject model derivation unit 21, the latent variable derivation unit 22, and the virtual image derivation unit 23, respectively, but the first network 31, the second network 32, and the third network 33 configure the image generation model according to the present disclosure.

FIG. 3 is a schematic diagram showing a configuration of the image generation model. As shown in FIG. 3, an image generation model 30 includes the first network 31, the second network 32, and the third network 33. The first network 31 includes a convolutional neural network (CNN) 31A and a combining unit 31B. The CNN 31A is hierarchically connected with a plurality of convolutional layers and pooling layers. The convolutional layer performs convolution processing using various kernels on the input image, and outputs a feature amount map including the feature amount obtained by the convolution processing. The kernel has an n×n pixel size (for example, n=3), and a weight is set for each element. Specifically, the weight, such as a differential filter that emphasizes the edge of the input image, are set. The convolutional layer applies the kernel to the entire input image or the feature amount map output from the processing layer in the previous stage while shifting an attention pixel of the kernel. Further, the convolutional layer applies an activation function, such as a sigmoid function, to a convolved value, and outputs the feature amount map.

The pooling layer reduces an amount of data in the feature amount map by pooling the feature amount map output by the convolutional layer, and outputs the feature amount map with the reduced amount of data.

Note that the subsequent processing layer outputs the feature amount map while up-sampling the feature amount map.

Moreover, by repeating the outputting, pooling, and up-sampling of the feature amount map in each processing layer, the feature amount for each pixel of the input target image Gi is output as a feature vector from the final layer of the CNN 31A. The feature vector is a one-dimensional vector having n elements. In the present embodiment, in a case in which only one target image Gi is input to the first network 31, the output feature vector itself is the subject model M0.

Figure 4:
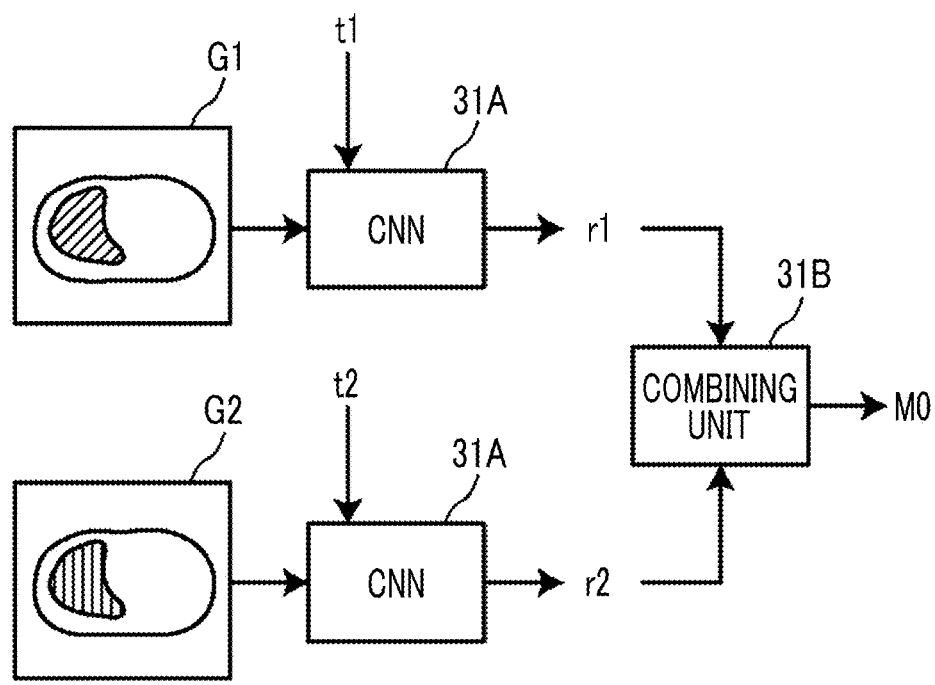
FIG. 4 is a diagram for describing generation of a subject model.

On the other hand, in a case in which two target images Gi are input to the first network 31, the subject model M0 is derived by combining feature vectors r1 and r2 output for each of two target images (referred to as a first target image G1 and a second target image G2) by the combining unit 31B. FIG. 4 is a diagram for describing the generation of the subject model M0 by combining. As shown in FIG. 4, it is assumed that the first and second target images G1 and G2, and the information t1 and t2 representing the representation formats thereof are input to the CNN 31A of the first network 31, the first feature vector r1 (a1, a2, . . . , an) is derived in certain pixel x of the first target image G1, and the second feature vector r2 (b1, b2, . . . , bn) is derived in the pixel of the second target image G2 corresponding to the pixel x.

The combining unit 31B derives the subject model M0 by adding the corresponding elements of the first feature vector r1 and the second feature vector r2 between the corresponding pixels of the first target image G1 and the second target image G2. The subject model M0 has the same number of pixels as the input target image Gi, and a composite feature vector is assigned to each pixel. Note that, instead of addition, two feature vectors r1 and r2 may be combined by deriving representative values, such as an average value and a median value, between the corresponding elements of two feature vectors r1 and r2. Here, in FIG. 4, two CNNs 31A are shown side by side, but the number of CNNs 31A included in the first network 31 may be only one or plural. In a case in which there are a plurality of the CNNs 31A, each of the plurality of CNNs 31A is constructed by the same learning.

Note that, in the present embodiment, in a case in which the plurality of target images Gi are used, the plurality of target images Gi are normalized. That is, registration processing of aligning the sizes and spatial positions of the subjects included in the target images Gi, smoothing processing of removing fine structural differences and noise, and the like are performed.

Figure 5:
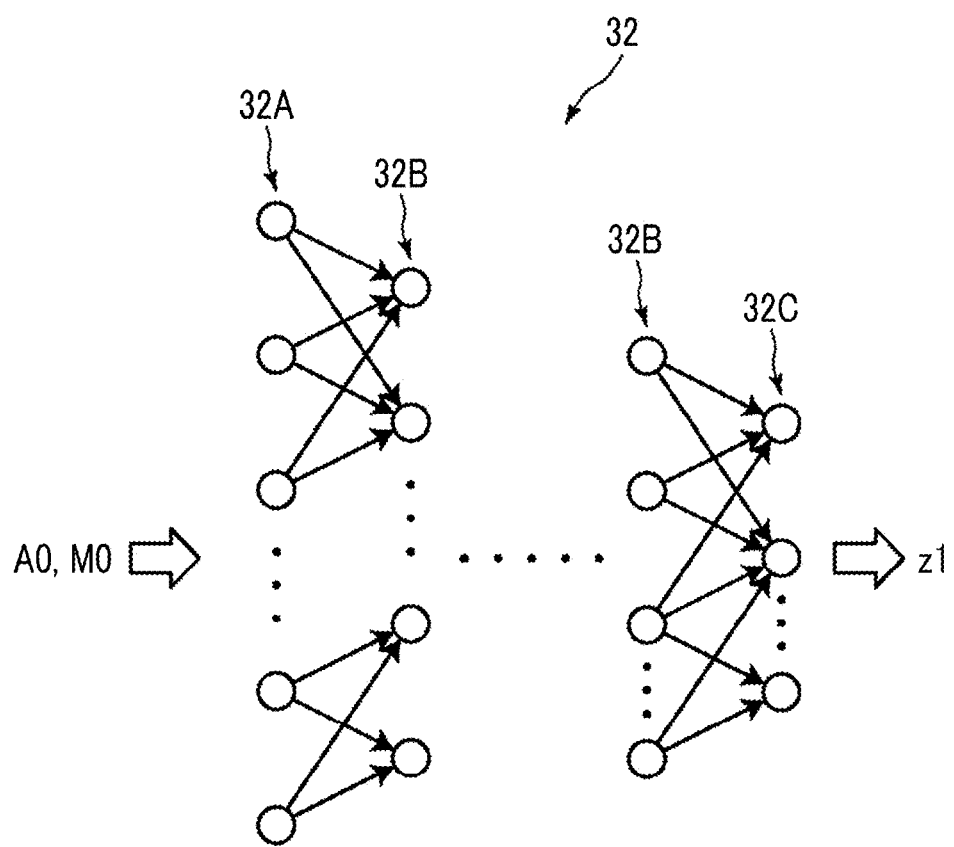
FIG. 5 is a diagram showing a configuration of a second network.

In a case in which the target information A0 and the subject model M0 are input, the second network 32 outputs the first latent variable z1 obtained by dimensionally compressing the feature of the subject model M0 according to the target information A0. The second network 32 includes a convolutional neural network, which is one of the multi-layer neural networks in which a plurality of processing layers are hierarchically connected, but unlike the CNN 31A of the first network 31, has a function as encoder that dimensionally compresses the feature of the input subject model M0 according to the target information A0. FIG. 5 is a diagram for describing the second network. As shown in FIG. 5, the second network 32 includes an input layer 32A, at least one interlayer 32B, and an output layer 32C, and the dimension of the output layer 32C is smaller than the dimension of the input layer 32A.

Moreover, in a case in which the target information A0 and the subject model M0 are input to the input layer 32A, the second network 32 performs processing of reducing (compressing) an information amount of the information representing the feature of the subject model M0 such that the virtual image V0 having the target representation format represented by the target information A0 can be derived, and outputs the latent variable z1 from the output layer 32C. The latent variable z1 represents the feature of the subject model M0, but includes the information having a smaller number of dimensions than the subject model M0. As a result, the latent variable z1 obtained by dimensionally compressing the feature of the subject model M0 according to the input target information A0 is output from the second network 32.

Figure 6:
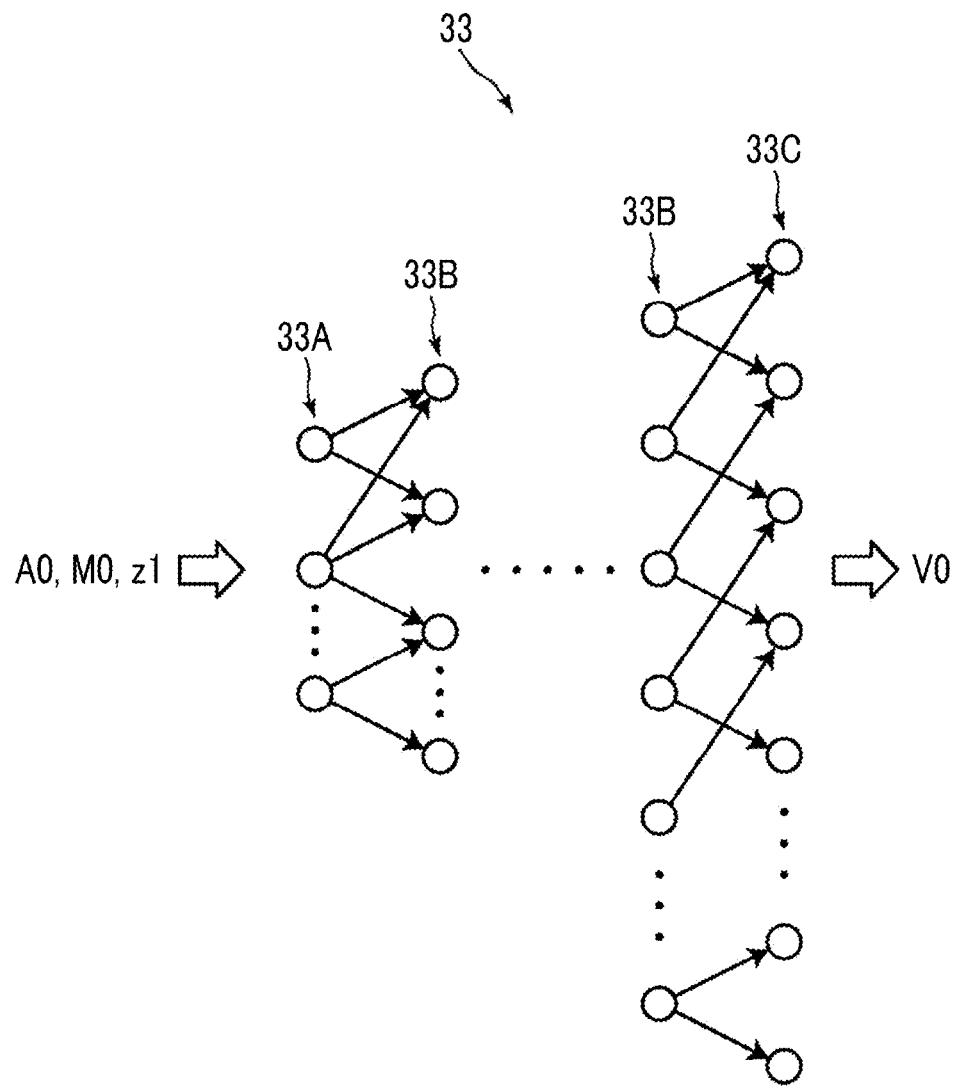
FIG. 6 is a diagram showing a configuration of a third network.

In a case in which the target information A0, the subject model M0, and the latent variable z1 are input, the third network 33 outputs the virtual image V0 having the target representation format represented by the target information A0. The third network 33 includes a convolutional neural network, which is one of a multi-layer neural network in which a plurality of processing layers are hierarchically connected, and has a function as decoder that reconstructs the virtual image V0 by reconstructing the input subject model M0 and the latent variable z1. FIG. 6 is a diagram for describing the third network. As shown in FIG. 6, the third network 33 includes an input layer 33A, at least one interlayer 33B, and an output layer 33C, and the dimension of the output layer 33C is larger than the dimension of the input layer 33A.

Moreover, in a case in which the target information A0, the subject model M0, and the latent variable z1 are input, the third network 33 performs processing of reconstructing the virtual image V0, and outputs the virtual image V0 from the output layer 33C. As a result, the virtual image V0 having the target representation format is output from the third network 33.

The learning unit 25 trains the image generation model 30 by using the plurality of teacher data. That is, the learning unit 25 trains the first network 31 of the subject model derivation unit 21, the second network 32 of the latent variable derivation unit 22, and the third network 33 of the virtual image derivation unit 23. For this purpose, the learning unit 25 includes a fourth network 34 that, in a case in which an image of a certain representation format is input for learning, outputs a latent variable z2 obtained by dimensionally compressing the feature of the image of the representation format. The fourth network 34 has a function as the encoder and has a configuration similar to that of the second network 32. The latent variable z2 represents the feature of the input image, but includes the information having a smaller number of dimensions than the input image.

In the present embodiment, the fourth network 34 is used only at the time of learning. Therefore, in the present embodiment, the learning unit 25 includes the fourth network 34, but the learning unit 25 is not limited to this. Note that it is assumed that the latent variable z1 output by the second network 32 is referred to as a first latent variable, and the latent variable z2 output by the fourth network 34 is referred to as a second latent variable. In addition, it is assumed that the dimensions of the first latent variable z1 and the second latent variable z2 are the same.

Figure 7:
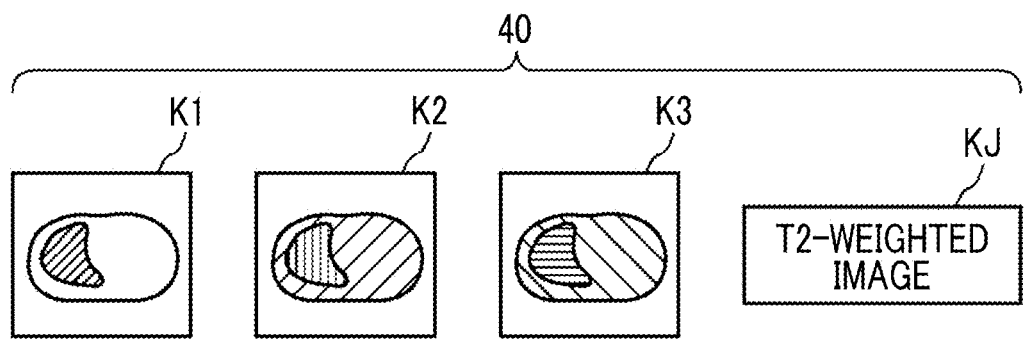
FIG. 7 is a diagram showing an example of teacher data.

FIG. 7 is a diagram showing an example of the teacher data. Teacher data 40 shown in FIG. 7 includes three teacher images K1 to K3 as an example. The type of image of the teacher image K1 is the CT image, the type of image of the teacher image K2 is the T1-weighted image of MRI, and the type of image of the teacher image K3 is the T2-weighted image of MRI. In addition, the teacher data 40 includes teacher information KJ representing the representation format for the teacher image K3. In the present embodiment, since the teacher information KJ is the T2-weighted image, the teacher information KJ represents the type of image of the T2-weighted image as the representation format. Note that the teacher data 40 may include information representing the type of image of the teacher images K1 and K2, that is, the representation formats. In the present embodiment, the teacher data 40 includes the information representing the type of image of the teacher images K1 and K2, that is, the representation formats. The plurality of teacher images included in one teacher data are acquired by imaging the same site of the same subject in the modality 2 such that images having different representation formats are acquired. For example, the teacher image K1 which is the CT image is acquired by the CT apparatus 2A, and the teacher image K2 which is the T1-weighted image and the teacher image K3 which is the T2-weighted image are acquired by the MRI apparatus 2B, respectively. Here, in FIG. 7, a difference in the representation format of the teacher images K1 to K3 is represented by giving different hatching to the teacher images K1 to K3.

Note that a plurality of the teacher images K1 to K3 are normalized for learning. That is, registration processing of aligning the spatial positions of the plurality of teacher images K1 to K3, smoothing processing of removing fine structural differences and noise, and the like are performed.

Figure 8:
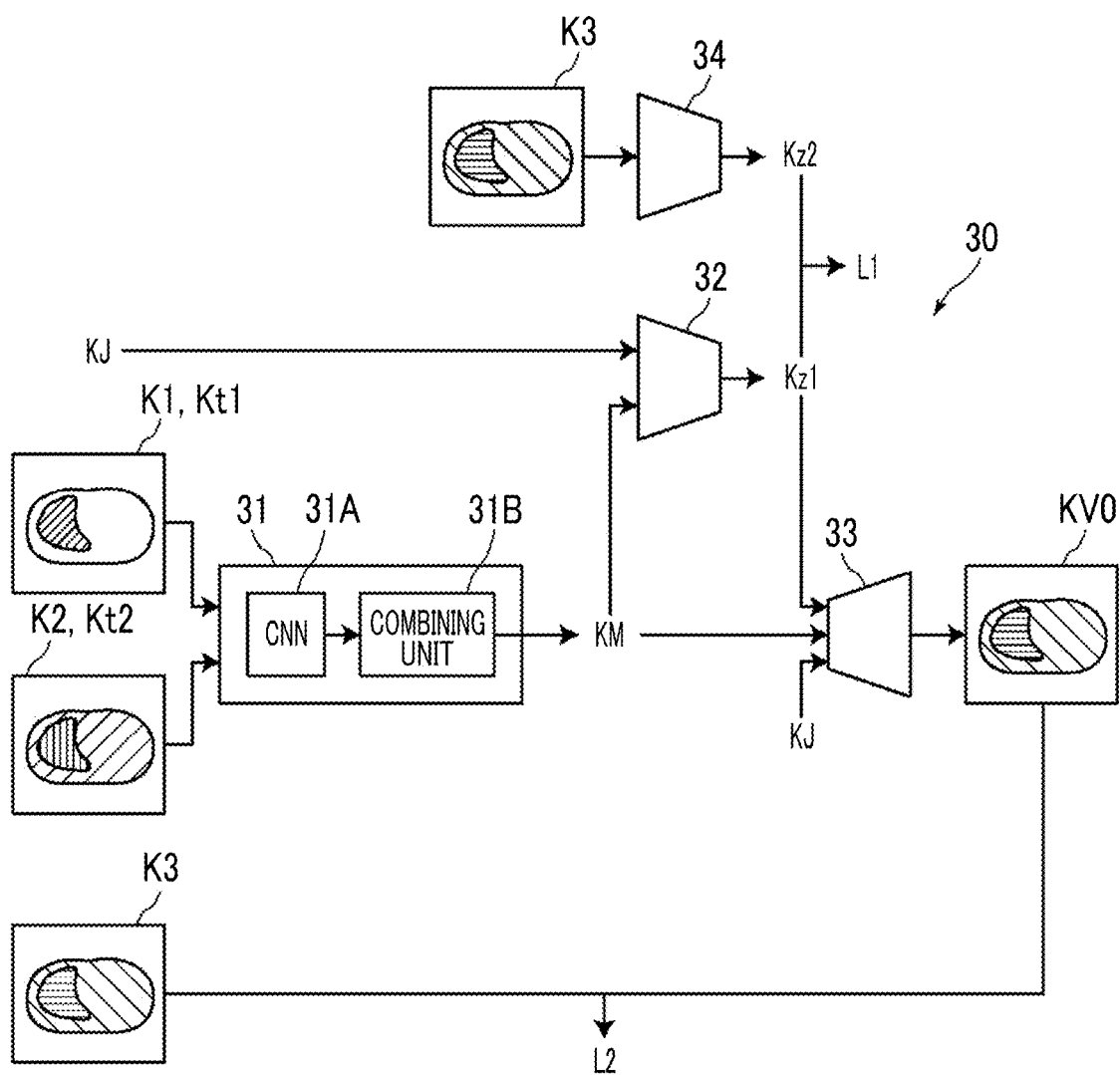
FIG. 8 is a conceptual diagram of learning of the image generation model.

FIG. 8 is a conceptual diagram of learning of the image generation model. First, the teacher image included in the teacher data 40 is input to the first network 31 at the time of learning. Specifically, the teacher image other than the teacher image having the representation format represented by the teacher information KJ is input. For example, in the teacher data 40 shown in FIG. 7, the teacher information KJ represents the representation format of the T2-weighted image. Therefore, the teacher image K1 which is the CT image and the teacher image K2 which is the T1-weighted image other than the teacher image K3 which is the T2-weighted image included in the teacher data 40 are input to the first network 31. Note that information Kt1 and Kt2 representing the representation formats of the teacher images K1 and K2 are also input to the first network 31. As a result, a feature vector for the teacher image K1 and a feature vector for the teacher image K2 are output from the CNN 31A of the first network 31. Moreover, two feature vectors are combined by the combining unit 31B, and a teacher subject model KM is derived.

In addition, the teacher information KJ included in the teacher data 40 shown in FIG. 7 and the teacher subject model KM output from the first network 31 are input to the second network 32. As a result, the second network 32 outputs a first teacher latent variable Kz1, which is the first latent variable z1 obtained by dimensionally compressing the feature of the teacher subject model KM according to the teacher information KJ.

In addition, the teacher information KJ included in the teacher data 40 shown in FIG. 7, the teacher subject model KM output from the first network 31, and the first teacher latent variable Kz1 output from the second network 32 are input to the third network 33. As a result, the third network 33 outputs a teacher virtual image KV0 having the representation format represented by the teacher information KJ, that is, the representation format of the T2-weighted image.

In addition, the teacher image K3 (here, the T2-weighted image) having the representation format corresponding to the teacher information KJ included in the teacher data 40 shown in FIG. 7 is input to the fourth network 34. As a result, the fourth network 34 outputs a second teacher latent variable Kz2, which is the second latent variable z2 obtained by dimensionally compressing the feature of the teacher image K3.

Moreover, the learning unit 25 derives a difference between the first teacher latent variable Kz1 and the second teacher latent variable Kz2 as a first loss L1. Moreover, the first network 31 and the second network 32 are trained by using the first loss L1. Here, the first teacher latent variable Kz1 output from the second network 32 is derived based on the teacher information KJ and the teacher subject model KM. Therefore, the first teacher latent variable Kz1 is different from the second teacher latent variable Kz2 output from the fourth network 34 based on the teacher image K3 having the representation format represented by the teacher information KJ, but a more preferable virtual image V0 can be output from the third network 33 as the difference between the first teacher latent variable Kz1 and the second teacher latent variable Kz2 is smaller.

For this purpose, in the present embodiment, the learning unit 25 trains the CNN 31A of the first network 31 and the second network 32 to reduce the first loss L1. Specifically, regarding the CNN 31A, the learning unit 25 trains the CNN 31A by deriving the number of convolutional layers and the number of pooling layers, which configure the CNN 31A, a coefficient of the kernel, magnitude of the kernel, and a weight of the bond between the layers in the convolutional layer such that the first loss L1 is equal to or less than a predetermined threshold value Th1. In addition, regarding the second network 32, the learning unit 25 trains the second network 32 by deriving the number of convolutional layers and the number of pooling layers, which configure the second network 32, a coefficient of the kernel, magnitude of the kernel, and a weight of the bond between the layers in the convolutional layer such that the first loss L1 is equal to or less than the predetermined threshold value Th1.

As a result, in a case in which at least one target image Gi is input, the first network 31 can output the subject model M0 in which the second network 32 can output the first latent variable z1 capable of deriving the virtual image V0 having the target representation format. In addition, in a case in which the subject model M0 output by the first network 31 is input, the second network 32 outputs the first latent variable z1 capable of outputting the virtual image V0 having the target representation format by the third network 33. Note that the learning unit 25 may perform learning a predetermined number of times instead of learning such that the first loss L1 is equal to or less than the predetermined threshold value Th1.

In addition, the learning unit 25 derives a difference between the teacher virtual image KV0 output by the third network 33 and the teacher image K3 having the representation format represented by the teacher information KJ as a second loss L2. Moreover, the first network 31, the second network 32, and the third network 33 are trained by using the second loss L2. Here, the teacher virtual image KV0 output from the third network 33 is derived based on the teacher information KJ, the teacher subject model KM, and the first teacher latent variable Kz1. Therefore, the teacher virtual image KV0 is different from the teacher image K3 having the representation format represented by the teacher information KJ, but a more preferable virtual image V0 can be output from the third network 33 as the difference between the teacher virtual image KV0 and the teacher image K3 is smaller.

For this purpose, in the present embodiment, the learning unit 25 trains the CNN 31A of the first network 31, the second network 32, and the third network 33 to reduce the second loss L2. Specifically, regarding the CNN 31A, the learning unit 25 trains the CNN 31A by deriving the number of convolutional layers and the number of pooling layers, which configure the CNN 31A, a coefficient of the kernel, magnitude of the kernel, and a weight of the bond between the layers in the convolutional layer such that the second loss L2 is equal to or less than a predetermined threshold value Th2. Note that the CNN 31A is trained based on both the first loss L1 and the second loss L2.

In addition, regarding the second network 32, the learning unit 25 trains the second network 32 by deriving the number of convolutional layers and the number of pooling layers, which configure the second network 32, a coefficient of the kernel, magnitude of the kernel, and a weight of the bond between the layers in the convolutional layer such that the second loss L2 is equal to or less than the predetermined threshold value Th2. Note that the second network 32 is also trained based on both the first loss L1 and the second loss L2.

In addition, regarding the third network 33, the learning unit 25 trains the third network 33 by deriving the number of convolutional layers and the number of pooling layers, which configure the third network 33, a coefficient of the kernel, magnitude of the kernel, and a weight of the bond between the layers in the convolutional layer such that the second loss L2 is equal to or less than the predetermined threshold value Th2.

As a result, the CNN 31A of the first network 31 outputs the subject model M0 in which the second network 32 can output the first latent variable z1 capable of deriving the virtual image V0 having the representation format represented by the target information A0 and the third network 33 can output the virtual image V0 having the target representation format. In addition, the second network 32 outputs the first latent variable z1 capable of outputting the virtual image V0 having the target representation format by the third network 33. In addition, in a case in which the target information A0, the subject model M0 output by the first network 31, and the first latent variable z1 output by the second network 32 are input, the third network 33 outputs the virtual image V0 having the target representation format.

Here, examples of the teacher image used as the teacher data include the CT image acquired by the CT apparatus 2A as described above, the T1-weighted image and the T2-weighted image acquired by the MRI apparatus 2B, and an image of any other type. For example, examples of the MRI image included in one teacher data include, in addition to the T1-weighted image and the T2-weighted image, the MRI image of any type, such as a diffusion-weighted image, a fat suppression image, an FLAIR image, a pre-contrast T1-weighted image, a post-contrast T1-weighted image, a T1-weighted image (in phase), a T1-weighted image (out phase), and a T2-fat suppression image. In this case, the teacher information KJ representing the type of image, such as the CT image and the MRI image, as the representation format need only be used.

By using such CT images and MRI images having various representation formats as the teacher images and using the teacher information KJ representing the type of image, such as the CT image and the MRI image as the representation format, in a case in which at least one target image Gi having any representation format and the target information A0 representing the representation format used as the teacher information KJ are input to the image generation device 1, the virtual image V0 having the representation format represented by the target information A0 is generated. For example, in a case in which the target image Gi is the CT image and the T1-weighted image of MRI, and the representation format represented by the target information A0 is the T2-weighted image of MRI, the virtual image V0 having the representation format of the T2-weighted image of MRI can be generated from the CT image and the T1-weighted image.

Figure 9:
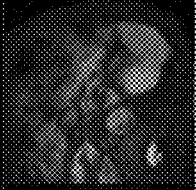
FIG. 9 is a diagram showing a representation format of a target image to be input and a representation format of a virtual image to be output.

FIG. 9 is a diagram showing a representation format of the target image to be input and the representation format of the virtual image to be output. Note that, in FIG. 9, the left column is the target image to be input, and the types of image as the representation format are, in order from the top, the post-contrast T1-weighted image, the T1-weighted image (out phase), the T2-weighted image, and the post-contrast T1-weighted image. In addition, the third to eighth columns from the left show the virtual images V0 having the converted representation format. The types of image as the representation format are the CT image, the post-contrast T1-weighted image, a T1 non-contrast image, the T1-weighted image (in phase), the T1-weighted image (out phase), and the T2-fat suppression image, respectively, in order from the third column on the left side. According to the present embodiment, as shown in FIG. 9, by using the teacher data in various representation formats, the virtual image V0 having the target representation format is generated regardless of the representation format of the target image Gi to be input.

Figure 10:
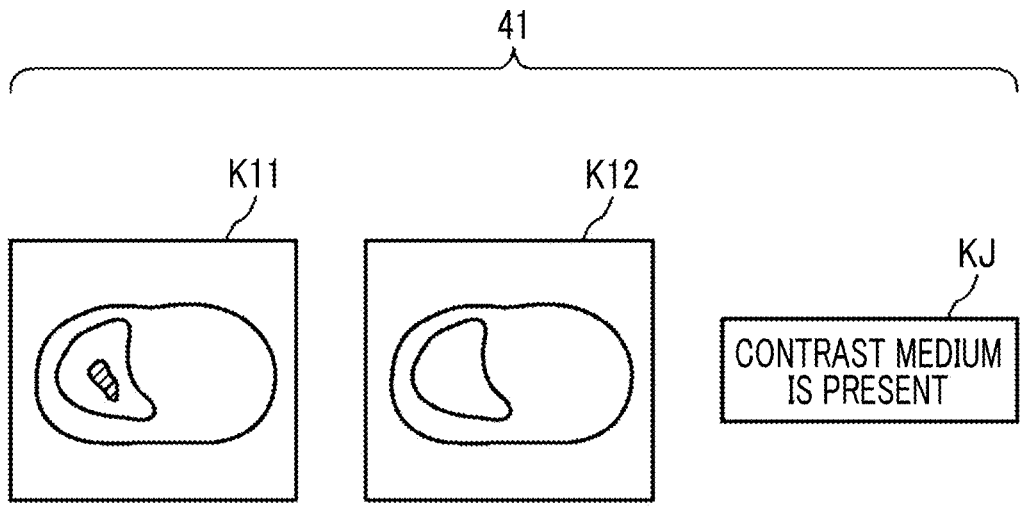
FIG. 10 is a diagram showing another example of the teacher data.

In addition, in a case in which performing CT imaging, there are a case in which the contrast medium is used and a case in which the contrast medium is not used. Therefore, as shown in FIG. 10, a CT image K11 acquired by using the contrast medium and a CT image K12 acquired without using the contrast medium can be included in one teacher data 41. In this case, the teacher information KJ representing the representation format of the presence or absence of the contrast medium in the CT image can be included in the teacher data 41. In FIG. 10, the teacher information KJ representing the representation format in which the contrast medium is present is included in the teacher data 41. In addition, in FIG. 10, a region of the contrast medium in the teacher image K11 is shown by hatching.

As described above, by learning the image generation model 30 by using the teacher data 41 including the CT image acquired by using the contrast medium and the CT image acquired without using the contrast medium as the teacher images K11 and K12, and including the teacher information KJ representing the representation format of the presence or absence of the contrast medium, in a case in which at least one target image Gi having any representation format and the target information A0 representing the representation format of the presence or absence of the contrast medium are input to the image generation device 1, the virtual image V0 having the representation format of contrast or non-contrast is generated according to the target information A0. For example, in a case in which the target image Gi is one non-contrast MRI image and the target information A0 represents that the contrast medium of CT is present, the image generation device 1 can generate the virtual image V0 having the representation format of the MRI image obtained by performing imaging using the contrast medium.

Figure 11:
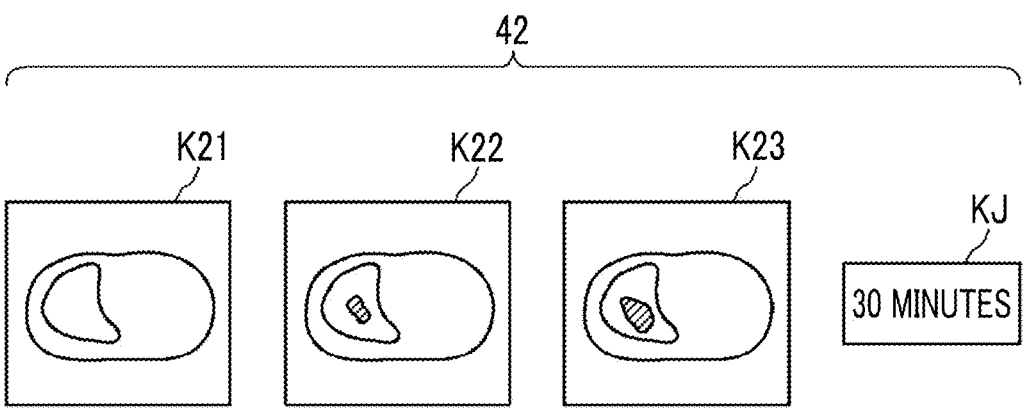
FIG. 11 is a diagram showing still another example of the teacher data.

In addition, in a case in which imaging is performed by using the contrast medium, as shown in FIG. 11, the plurality of CT images having different elapsed time after the injection of the contrast medium may be included in one teacher data 42 as teacher images K21 to K23. In this case, the teacher information KJ representing the representation format of the contrast phase, which represents the elapsed time after injection of the contrast medium in the CT image, need only be used. In FIG. 11, the teacher information KJ representing the representation format of 30 seconds as the contrast phase is included in the teacher data 42. In addition, in FIG. 11, the teacher image K21 is before contrast, the contrast phase of the teacher image K22 is, for example, 10 seconds, and the contrast phase of the teacher image K23 is 30 seconds.

As described above, by learning the image generation model 30 by using the teacher data 42 including the CT images having different elapsed time after the injection of the contrast medium as the teacher images K21 to K23 and including the teacher information KJ representing the representation format of the contrast phase, in a case in which at least one target image Gi having any representation format and the target information A0 representing the representation format of the contrast phase are input to the image generation device 1, the virtual image V0 having the representation format of the contrast phase according to the target information A0 is generated. For example, in a case in which the target image Gi is one non-contrast MRI image and the contrast phase represented by the target information A0 is 30 seconds, the image generation device 1 can generate the virtual image V0 having the representation format of the MRI image of 30 seconds after the injection of the contrast medium.

Figure 12:
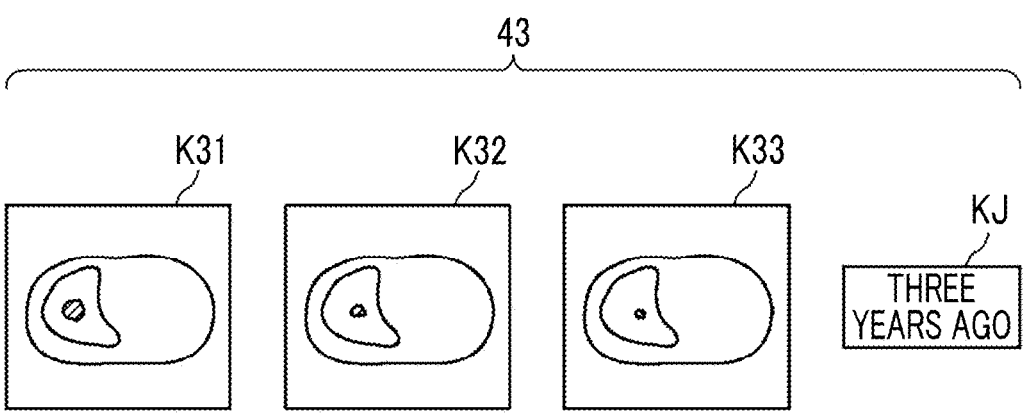
FIG. 12 is a diagram showing still another example of the teacher data.

In addition, in the present embodiment, as shown in FIG. 12, teacher data 43 including teacher images K31 to K33 having different imaging date and time can be used for the same site of the same subject. The teacher data 43 shown in FIG. 12 includes the CT image acquired by imaging on the same day, the CT image acquired by imaging one year ago, and the CT image acquired three years ago, for the same site of the same subject, as the teacher images K31 to K33, respectively. In this case, the teacher information KJ representing the representation format of the time before and after the current time (for example, one year ago, three years ago, one year later, or three years later) need only be used.

By learning the image generation model 30 by using the teacher data 43 including such images having different imaging date and time as the teacher images K31 to K33 and including the teacher information KJ representing the representation format of the time before and after the current time, in a case in which at least one target image Gi having any representation format and the target information A0 representing the representation format of the time before and after the current time are input to the image generation device 1, the virtual image V0 having the representation format of imaging period according to the target information A0 is generated. For example, in a case in which the target image Gi is one current MRI image and the representation format represented by the target information A0 is three years ago, the image generation device 1 can generate the virtual image V0 having the representation format of the MRI image three years ago.

Note that it is also possible to use a two-dimensional radiation image acquired by simple radiation as the teacher image used as the teacher data. However, all the teacher data need to be acquired by imaging the same site of the same subject.

Figure 13:
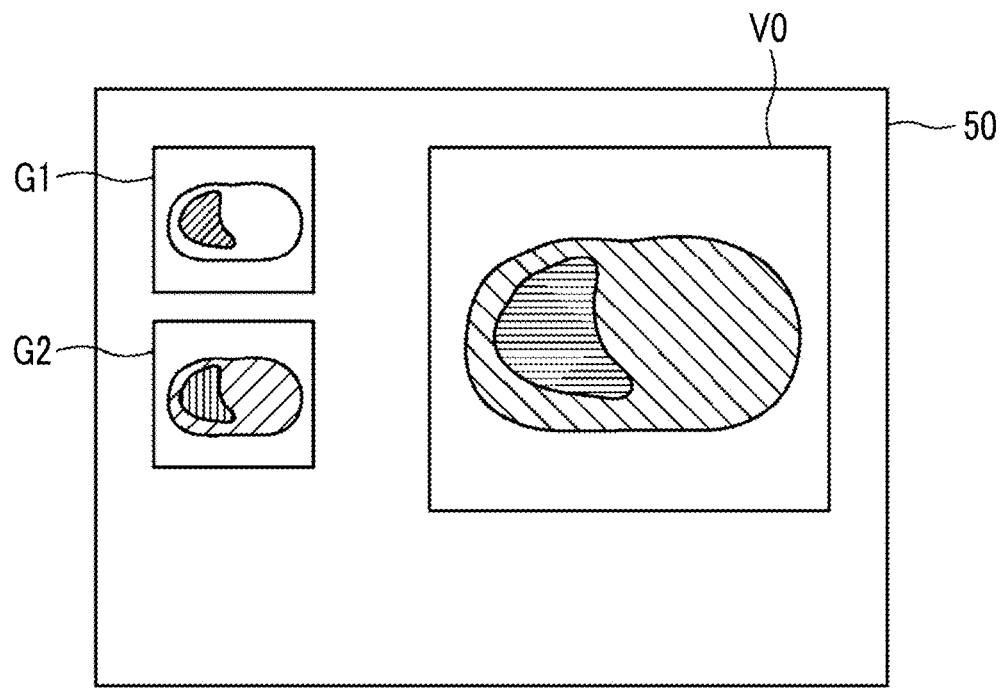
FIG. 13 is a diagram showing a display screen of a virtual image.

The display control unit 24 displays the virtual image V0 output by the virtual image derivation unit 23 on the display unit 14. FIG. 13 is a diagram showing a display screen of the virtual image V0. Note that, here, the description will be made that one virtual image V0 is generated from two target images G1 and G2. As shown in FIG. 13, two target images G1 and G2, and the virtual image V0 are displayed on a display screen 50. The target images G1 and G2 are, for example, the CT image and the T1-weighted image, respectively, and the virtual image V0 is the T2-weighted image.

Figure 14:
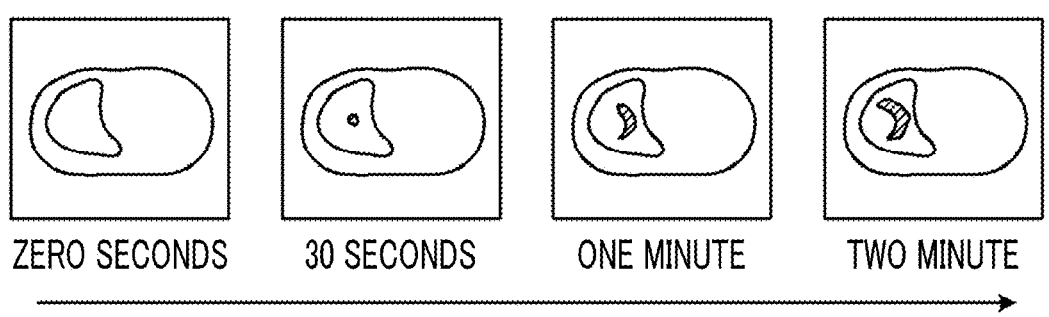
FIG. 14 is a diagram showing a plurality of virtual images having different contrast phases.

Note that by using the target information A0 representing the representation format of a plurality of the contrast phases, it is possible to generate a plurality of the virtual images V0 representing a state in which the contrast medium spreads. For example, as shown in FIG. 14, it is possible to generate the plurality of virtual images V0 in which an aspect of the spread of the contrast medium with the elapse of time of 30 seconds, one minute, and two minutes can be confirmed.

Figure 15:
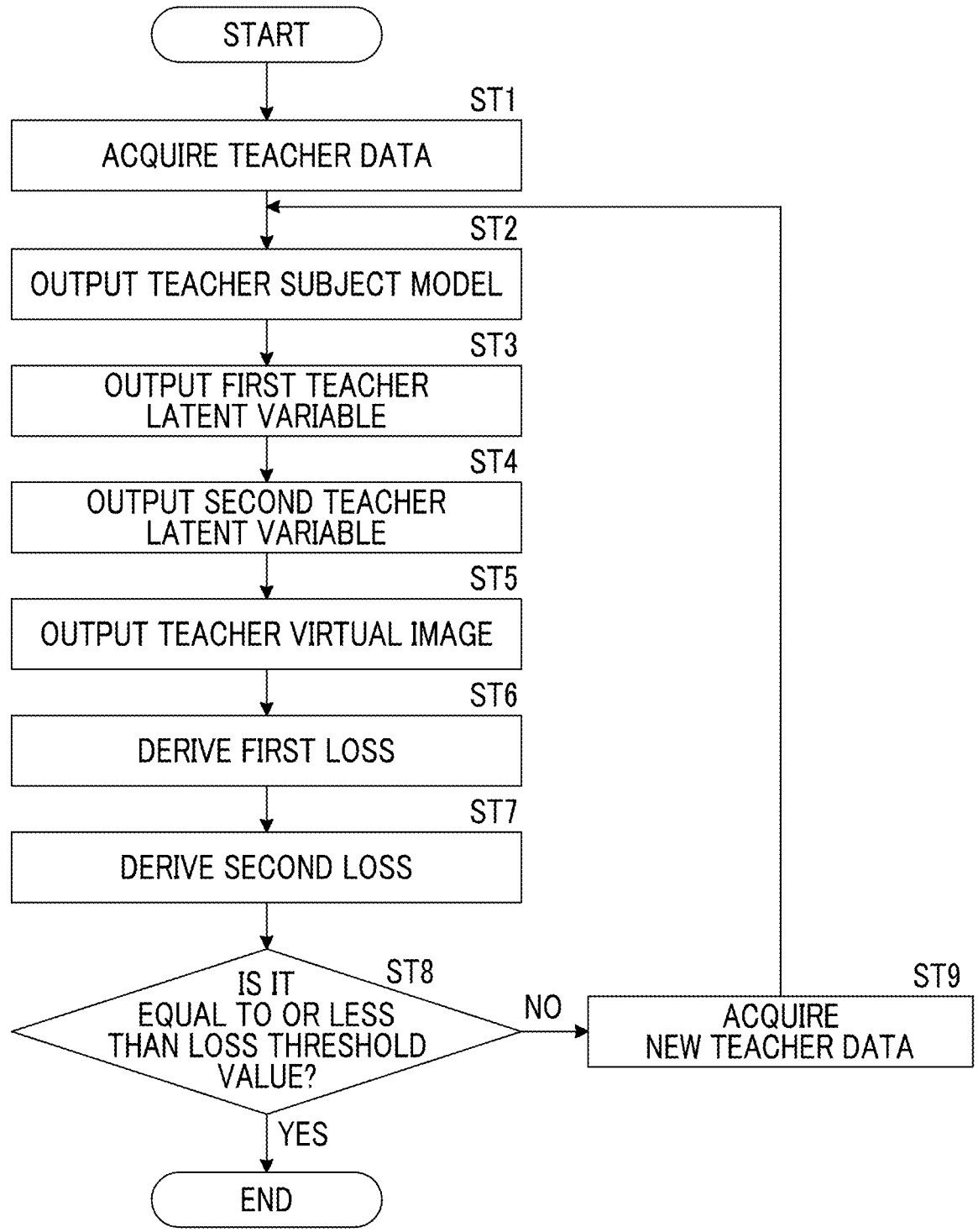
FIG. 15 is a flowchart of learning processing performed in the present embodiment.

Then, processing performed in the present embodiment will be described. FIG. 15 is a flowchart showing the learning processing performed in the present embodiment. Note that it is assumed that the plurality of teacher data are acquired from the image storage server 3 and stored in the storage 13. First, the learning unit 25 acquires one teacher data 40 from the storage 13 (step ST1), and inputs the teacher images K1 and K2, which are included in the teacher data 40, having the representation format other than the teacher image K3 having the representation format represented by the teacher information KJ, and the information Kt1 and Kt2 representing the representation format of the teacher images K1 and K2 to the first network 31. The first network 31 outputs the teacher subject model KM by deriving the feature amounts from the teacher images K1 and K2 and combining the feature amounts (step ST2). In addition, the learning unit 25 inputs the teacher subject model KM and the teacher information KJ to the second network 32. The second network 32 outputs the first teacher latent variable Kz1, which is the first latent variable z1 obtained by dimensionally compressing the feature of the teacher subject model KM according to the teacher information KJ (step ST3).

In addition, the learning unit 25 inputs the teacher image K3 in the representation format represented by the teacher information KJ to the fourth network 34. The fourth network 34 outputs the second teacher latent variable Kz2, which is the second latent variable z2 obtained by dimensionally compressing the feature of the teacher image K3 (step ST4). Further, the learning unit 25 inputs the teacher information KJ, the teacher subject model KM, and the first teacher latent variable Kz1 to the third network 33. The third network 33 outputs the teacher virtual image KV0 having the representation format represented by the teacher information KJ (step ST5). Note that the processing of step ST4 may be performed in parallel with or before or after any of the processing of steps ST1 to ST3, and step ST5.

Then, the learning unit 25 derives the difference between the first teacher latent variable Kz1 and the second teacher latent variable Kz2 as the first loss L1 (step ST6). In addition, the learning unit 25 derives the difference between the teacher virtual image KV0 and the teacher image K3 as the second loss L2 (step ST7). Moreover, the learning unit 25 determines whether or not the first loss L1 and the second loss L2 are equal to or less than the predetermined threshold values Th1 and Th2, respectively (equal to or less than a loss threshold value; step ST8). In a case in which a negative determination is made in step ST8, the learning unit 25 acquires new teacher data from the storage 13 (step ST9), returns to the processing of step ST1, and repeats the processing of steps ST1 to ST8 by using the new teacher data. In a case in which a positive determination is made in step ST8, the learning unit 25 terminates the learning processing. As a result, the image generation model 30 is constructed.

Figure 16:
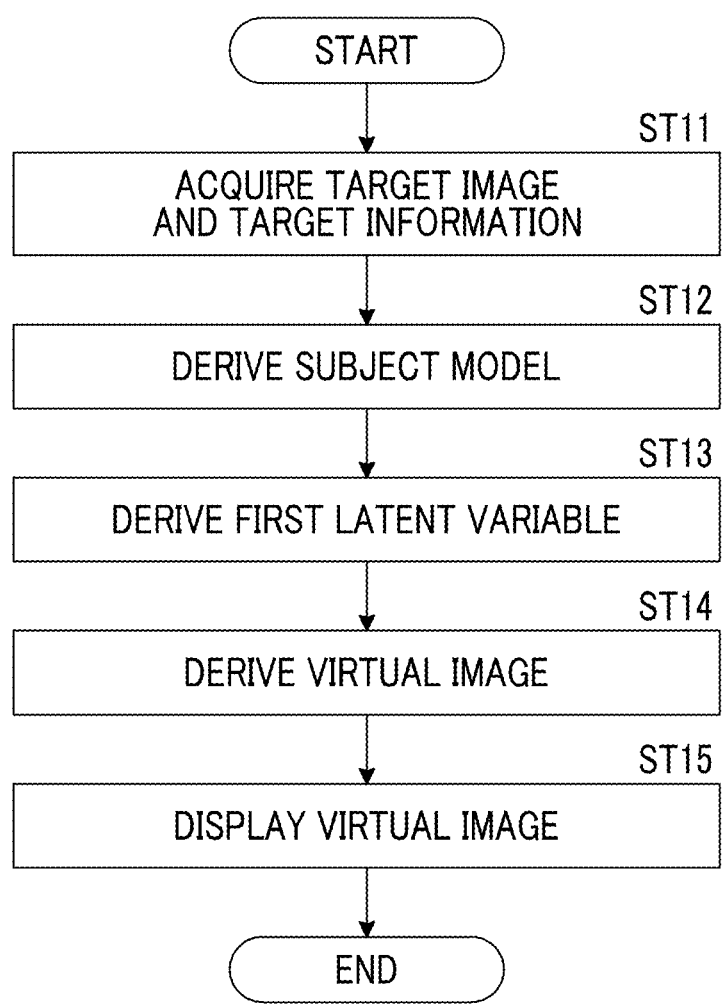
FIG. 16 is a flowchart showing image generation processing performed in the present embodiment.

FIG. 16 is a flowchart showing the image generation processing performed in the present embodiment. Note that it is assumed that the target image Gi and the target information A0 are input from the input unit 15 or acquired from the image storage server 3, and stored in the storage 13. In response to the instruction to start the image generation processing, the information acquisition unit 20 acquires at least one target image Gi and the target information A0 from the storage 13 (step ST11). The subject model derivation unit 21 inputs at least one target image Gi and the information ti representing the representation format of the target image Gi to the first network 31. The first network 31 outputs the subject model M0 by deriving the feature amount of the target image Gi ad combining the feature amounts. As a result, the subject model derivation unit 21 derives the subject model M0 (step ST12).

In addition, the latent variable derivation unit 22 inputs the target information A0 and the subject model M0 to the second network 32. The second network 32 outputs the first latent variable z1 obtained by dimensionally compressing the feature of the subject model M0 according to the target information A0 in a case in which the target information A0 and the subject model M0 are input. As a result, the latent variable derivation unit 22 derives the first latent variable z1 (step ST13).

The virtual image derivation unit 23 inputs the target information A0, the subject model M0, and the first latent variable z1 to the third network 33. The third network 33 outputs the virtual image V0 having the representation format represented by the target information A0. As a result, the virtual image derivation unit 23 derives the virtual image V0 (step ST14). Moreover, the display control unit 24 displays the virtual image V0 on the display unit 14 (step ST15), and terminates the processing.

As described above, in the present embodiment, the first network 31 included in the subject model derivation unit 21 is trained such that the subject model M0 is output in which the second network 32 can output the first latent variable z1 capable of deriving the virtual image V0 having the representation format represented by the target information A0 and the third network 33 can output the virtual image V0 having the target representation format. In addition, the second network 32 included in the latent variable derivation unit 22 is trained such that the first latent variable z1 capable of outputting the virtual image V0 having the target representation format by the third network 33 is output in a case in which the subject model M0 output by the first network 31 is input. In addition, the third network 33 included in the virtual image derivation unit 23 is trained such that the virtual image V0 having the target representation format is output in a case in which the target information A0, the subject model M0 output by the first network 31, and the first latent variable z1 output by the second network 32 are input.

As a result, the first network 31 of the subject model derivation unit 21 can be constructed such that the subject model M0 is output in which the second network 32 can output the first latent variable z1 capable of deriving the virtual image V0 having the representation format represented by the target information A0 and the third network 33 can output the virtual image V0 having the target representation format. In addition, the second network 32 of the latent variable derivation unit 22 can be constructed such that the first latent variable z1 capable of outputting the virtual image V0 having the target representation format by the third network 33 is output in a case in which the subject model M0 output by the first network 31 is input. In addition, the third network 33 of the virtual image derivation unit 23 can be constructed such that the virtual image V0 having the representation format represented by the target information A0 can be output from the target information A0, the subject model M0, and the first latent variable z1.

Therefore, according to the image generation device 1 according to the present embodiment, the virtual image V0 having the target representation format represented by the target information A0 can be derived from at least one target image Gi and the target information A0.

By the way, in a case in which the representation format of the image is converted to another representation format, there is a possibility that a unique feature of the original image is impaired. For example, in a case in which the target image Gi is the MRI image, in a case in which the representation format thereof is converted to the CT image, there is a possibility that a fine lesion and the like included in the MRI image disappear in the CT image. Here, it is possible to increase the information of the image that is the source for deriving the virtual image V0 by inputting the plurality of target images Gi to the image generation device 1 according to the present embodiment. Therefore, by using the plurality of target images Gi, it is possible to reduce a possibility of information loss due to the conversion of the representation format.

Note that, in the embodiment described above, the target information A0 represents any of the type of image, the presence or absence of the contrast medium, the contrast phase in a case in which the contrast medium is present, or the time before and after the current time, but the present disclosure is not limited to this. The target information A0 representing at least one of the above as the representation format may be used. In addition, the target information A0 further representing the representation format, such as the gender of the subject and the age of the subject, may be used. In this case, the teacher information KJ included in the teacher data need only further include at least one of the gender of the subject or the age of the subject. As a result, an information amount of the target information A0 can be increased, so that a more preferable virtual image V0 can be generated. Note that as the target information A0, only information representing the gender of the subject or the age of the subject as the representation format may be used.

Note that, in the embodiment described above, the first network 31 outputs the subject model M0 by inputting the target image Gi and the information ti representing the representation format thereof, but the present disclosure is not limited to this. The first network 31 may be constructed such that the subject model M0 is output only by inputting the target image Gi.

In addition, in the embodiment described above, the subject model derivation unit 21, the latent variable derivation unit 22, and the virtual image derivation unit 23 include the first network 31, the second network 32, and the third network 33, which are trained by the learning unit 25, respectively, but the present disclosure is not limited to this. For example, it is possible to execute the processing in the subject model derivation unit 21, the latent variable derivation unit 22, and the virtual image derivation unit 23 by software, which is not the network constructed by learning.

In addition, in the embodiment described above, the image generation device 1 includes the learning unit 25, but the present disclosure is not limited to this. The learning device comprising the learning unit 25 may be provided separately from the image generation device 1, and the image generation model may be trained by the learning device provided separately. In this case, the image generation model constructed by learning is installed in the image generation device 1.

In addition, in the embodiment described above, the liver is the specific structure, but the present disclosure is not limited to this. In addition to the liver, a structure, such as lungs, heart, kidneys, and brain, can be used as the target image. Note that at the time of learning, the first network 31, the second network 32, and the third network 33 specialized for the target image Gi including the specific structure are constructed by using the teacher image including the specific structure included in the target image.

In addition, in the embodiment described above, for example, various processors shown below can be used as the hardware structures of processing units that execute various pieces of processing, such as the information acquisition unit 20, the subject model derivation unit 21, the latent variable derivation unit 22, the virtual image derivation unit 23, the display control unit 24, and the learning unit 25. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. As described above, as the hardware structure, various processing units are configured by one or more of various processors described above.

Further, as the hardware structures of these various processors, more specifically, it is possible to use an electrical circuit (circuitry) in which circuit elements such as semiconductor elements are combined.

What is claimed is:

1. A learning device of an image generation model that, in a case in which at least one target image for a subject, which includes a specific structure, having at least one representation format, and target information representing a target representation format of the target image are input, derives a virtual image having the target representation format from the target image, the learning device comprising at least one processor,
wherein the image generation model includes
a first network that outputs a subject model representing the subject by deriving each feature amount of the target image having the at least one representation format and combining the feature amounts by inputting the target image,
a second network that, in a case in which the target information and the subject model are input, outputs a latent variable obtained by dimensionally compressing a feature of the subject model according to the target information, and
a third network that, in a case in which the target information, the subject model, and the latent variable are input, outputs the virtual image, and
wherein the processor is configured to train the first network, the second network, and the third network based on a plurality of teacher images having different representation formats for the subject including the specific structure, and a plurality of teacher data including specific teacher information representing a specific representation format among representation formats of the plurality of teacher images.

2. The learning device according to claim 1,
wherein the first network outputs the subject model representing the subject by deriving each feature amount of the target image and combining the feature amounts by inputting information representing the representation format of the target image in addition to the target image.

3. The learning device according to claim 1, further comprising:
a fourth network that, in a case in which an image is input, outputs a latent variable obtained by dimensionally compressing a feature of the image,
wherein the processor is configured to:
input another teacher image having a representation format other than the specific representation format among the plurality of teacher images included in the teacher data to the first network to output a teacher subject model,
input the specific teacher information and the teacher subject model to the second network to output a first teacher latent variable obtained by dimensionally compressing a feature of the teacher subject model according to the specific teacher information,
input a specific teacher image having the specific representation format to the fourth network to output a second teacher latent variable obtained by dimensionally compressing a feature of the specific teacher image, and
train the first network and the second network by using a difference between the first teacher latent variable and the second teacher latent variable as a first loss.

4. The learning device according to claim 3,
wherein the processor is configured to:
input the specific teacher information, the teacher subject model, and the first teacher latent variable to the third network to output a teacher virtual image having the specific representation format, and
train the first network, the second network, and the third network by using a difference between the teacher virtual image and the specific teacher image as a second loss.

5. The learning device according to claim 1,
wherein the target information represents at least one of a type of image, presence or absence of a contrast medium, a contrast phase in a case in which a contrast medium is present, time before and after current time, gender of the subject, or age of the subject as the representation format.

6. The learning device according to claim 1,
wherein the target image is a three-dimensional medical image, and
the representation format includes at least one type of image of a CT image, an MRI image, or a PET image.

7. The learning device according to claim 6,
wherein the type of image includes at least one of a T1-weighted image, a T2-weighted image, a diffusion-weighted image, a fat suppression image, an FLAIR image, a pre-contrast T1-weighted image, a post-contrast T1-weighted image, a T1-weighted image (in phase), a T1-weighted image (out phase), or a T2-fat suppression image in the MRI image.

8. An image generation model trained by the learning device according to claim 1.

9. A learning method of an image generation model that, in a case in which at least one target image for a subject, which includes a specific structure, having at least one representation format, and target information representing a target representation format of the target image are input, derives a virtual image having the target representation format from the target image,
wherein the image generation model includes
a first network that outputs a subject model representing the subject by deriving each feature amount of the target image having the at least one representation format and combining the feature amounts by inputting the target image,
a second network that, in a case in which the target information and the subject model are input, outputs a latent variable obtained by dimensionally compressing a feature of the subject model according to the target information, and
a third network that, in a case in which the target information, the subject model, and the latent variable are input, outputs the virtual image, and
the learning method comprises:
learning the first network, the second network, and the third network based on a plurality of teacher images having different representation formats for the subject including the specific structure, and a plurality of teacher data including specific teacher information representing a specific representation format among representation formats of the plurality of teacher images.

10. A non-transitory computer-readable storage medium that stores a learning program causing a computer to execute a learning method of an image generation model that, in a case in which at least one target image for a subject, which includes a specific structure, having at least one representation format, and target information representing a target representation format of the target image are input, derives a virtual image having the target representation format from the target image, wherein the image generation model includes
a first network that outputs a subject model representing the subject by deriving each feature amount of the target image having the at least one representation format and combining the feature amounts by inputting the target image,
a second network that, in a case in which the target information and the subject model are input, outputs a latent variable obtained by dimensionally compressing a feature of the subject model according to the target information, and
a third network that, in a case in which the target information, the subject model, and the latent variable are input, outputs the virtual image, and
the learning program causing the computer to execute:
a procedure of learning the first network, the second network, and the third network based on a plurality of teacher images having different representation formats for the subject including the specific structure, and a plurality of teacher data including specific teacher information representing a specific representation format among representation formats of the plurality of teacher images.

\* \* \* \* \*